United States Patent
Zala et al.

(10) Patent No.: US 11,273,126 B2
(45) Date of Patent: Mar. 15, 2022

(54) AMORPHOUS DISPERSION OF CYCLOPROPANECARBOXYLIC ACID (5-{5-[N'-(2-CHLORO-6-METHYLBENZOYL) HYDRAZINOCARBONYL]-2-METHYL-PHENYLETHYNYL}-PYRIDIN-2-YL) AMIDE

(71) Applicant: SUN PHARMA ADVANCED RESEARCH COMPANY LIMITED, Maharashtra (IN)

(72) Inventors: Yashoraj Zala, Maharashtra (IN); Bramhanand Hanamannavar, Maharashtra (IN); Nitin Dharmadhikari, Maharashtra (IN)

(73) Assignee: SUN PHARMA ADVANCED RESEARCH COMPANY LIMITED, Maharashtra (IN)

( * ) Notice: Subject to any disclaimer, the term of this patent is extended or adjusted under 35 U.S.C. 154(b) by 118 days.

(21) Appl. No.: 16/494,598

(22) PCT Filed: Mar. 15, 2018

(86) PCT No.: PCT/IN2018/050147
§ 371 (c)(1),
(2) Date: Sep. 16, 2019

(87) PCT Pub. No.: WO2018/167803
PCT Pub. Date: Sep. 20, 2018

(65) Prior Publication Data
US 2021/0113470 A1  Apr. 22, 2021

(30) Foreign Application Priority Data
Mar. 15, 2017  (IN) .............................. 201721005409

(51) Int. Cl.
*A61K 9/16*  (2006.01)
*A61K 9/00*  (2006.01)
*A61K 31/44*  (2006.01)

(52) U.S. Cl.
CPC .......... *A61K 9/1635* (2013.01); *A61K 9/0053* (2013.01); *A61K 9/1641* (2013.01); *A61K 31/44* (2013.01); *C07B 2200/13* (2013.01)

(58) Field of Classification Search
CPC .. A61K 9/1635; A61K 9/0053; A61K 9/1641; A61K 31/44; C07B 2200/13
See application file for complete search history.

(56) References Cited

U.S. PATENT DOCUMENTS

| | | | | |
|---|---|---|---|---|
| 9,024,021 B2* | 5/2015 | Sengupta | ............. | C07D 213/56 544/236 |
| 2011/0288090 A1* | 11/2011 | Armstrong | ........... | C07D 475/04 514/234.2 |
| 2013/0225567 A1* | 8/2013 | Reiser | .................. | C07D 413/14 514/230.5 |
| 2013/0296557 A1* | 11/2013 | Sengupta | ................ | A61P 43/00 544/236 |
| 2014/0343086 A1* | 11/2014 | Dodd | ................... | C07D 403/10 514/275 |
| 2015/0152088 A1 | 6/2015 | Wang et al. | | |

FOREIGN PATENT DOCUMENTS

| | | |
|---|---|---|
| JP | 2010-509289 A | 3/2010 |
| JP | 2015-5036613 A | 2/2015 |
| JP | 2015-503613 A5 | 2/2016 |
| WO | 2007/075869 A2 | 7/2007 |
| WO | 2012/098416 A1 | 7/2012 |
| WO | WO 2015/128298 A1 | 9/2015 |
| WO | WO 2016/021707 A1 | 2/2016 |
| WO | 2016/185490 A1 | 11/2016 |
| WO | WO 2016/185490 A1 | 11/2016 |

OTHER PUBLICATIONS

Written Opinion dated May 16, 2018 for PCT Application No. PCT/IN2018/050147.
International Search Report (Revised) dated Jan. 29, 2019 for PCT Application No. PCT/IN2018/050147.
Dec. 11, 2020, European Search Report issued for related EP application No. 18768528.4.
Apr. 22, 2021, Australian Examination Report issued for related AU application No. 2018235447.
Jul. 13, 2021, Russian Office Action issued for related RU application No. 2019132074.
Guy Van Den Mooter, The use of amorphous solid dispersions: A formulation strategy to overcome poor solubility and dissolution rate, Drug Discovery Today: Technologies, Summer 2012, pp. e79-e85, vol. 9, No. 2.
Riikka Laitinen et al., Emerging trends in the stabilization of amorphous drugs, International Journal of Pharmaceutics, Apr. 28, 2012, pp. 65-79.

(Continued)

*Primary Examiner* — Robert A Wax
*Assistant Examiner* — Olga V. Tcherkasskaya
(74) *Attorney, Agent, or Firm* — Paratus Law Group, PLLC

(57) ABSTRACT

An oral, solid dosage form comprising a mixture of compound of formula I and a fusible polymeric carrier; and optionally pharmaceutically acceptable excipients, wherein the mixture is an amorphous dispersion.

Formula I

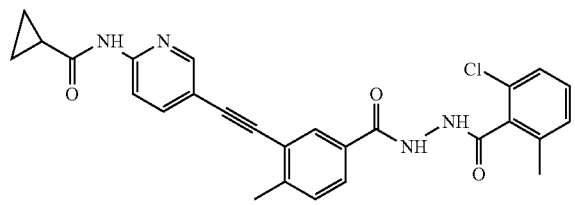

5 Claims, 4 Drawing Sheets

(56) References Cited

OTHER PUBLICATIONS

Anna Karagianni et al., Co-Amorphous Solid Dispersions for Solubility and Absorption Improvement of Drugs: Composition, Preparation, Characterization and Formulations for Oral Delivery, Pharmaceutics, Jul. 19, 2018, pp. 1-26.
Amorphous Formulations of Apixaban by Hot Melt Extrusion, Research Disclosure, Aug. 14, 2014, pp. 1-5.
Jan. 11, 2022, Japanese Office Action issued for related JP application No. 2019-550640.
Herbrink et al., Inherent formulation issues of kinase inhibitors, Journal of Controlled Release, Oct. 10, 2016, pp. 118-127, Elsevier.
Hardung et al., Combining HME & solubilization: Soluplus® The solid solution, Drug Delivery Technology, Apr. 2010, pp. 21-27.
Linn et al., Soluplus® as an effective absorption enhancer of poorly soluble drugs in vitro and in vivo, European Journal of Pharmaceutical Sciences, 2012, pp. 336-343, Elsevier.

\* cited by examiner

AMORPHOUS DISPERSION OF CYCLOPROPANECARBOXYLIC ACID (5-{5-[N'-(2-CHLORO-6-METHYLBENZOYL)HYDRAZINOCARBONYL]-2-METHYL-PHENYLETHYNYL}-PYRIDIN-2-YL) AMIDE

The PCT application WO2016/185490 discloses a compound of Formula I (cyclopropanecarboxylic acid (5-{5-[N-(2-chloro-6-methylbenzoyl) hydrazinocarbonyl]-2-methyl-phenylethynyl}-pyridin-2-yl)amide).

Formula I

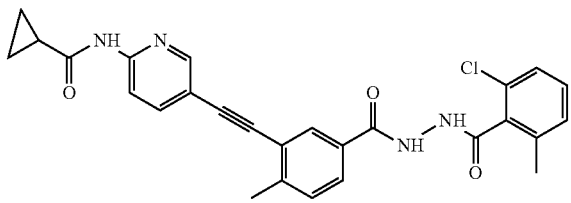

FIELD OF INVENTION

The present invention relates to amorphous dispersion of cyclopropanecarboxylic acid (5-{5-[N'-(2-chloro-6-methyl-benzoyl) hydrazinocarbonyl]-2-methyl-phenylethynyl}-pyridin-2-yl)amide.

BACKGROUND OF THE INVENTION

Compound of Formula I is a potent inhibitor of Abl tyrosine kinase. Conventional oral solid dosage forms of compound of Formula I failed to provide adequate bioavailability. There remains a need to provide the compound of formula I in a bioavailable form. There is a need for an oral solid dosage form of the compound of formula I that has adequate bioavailability and stability.

SUMMARY OF THE INVENTION

The present inventors have discovered novel amorphous dispersion of compound of Formula I in a fusible polymeric carrier and oral, solid dosage form comprising the amorphous dispersion. The oral, solid dosage form of the amorphous dispersion provides enhanced bioavailability as well as stability.

In a preferred embodiment, the present invention provides an oral, solid dosage form comprising a mixture of a compound of formula I Formula I

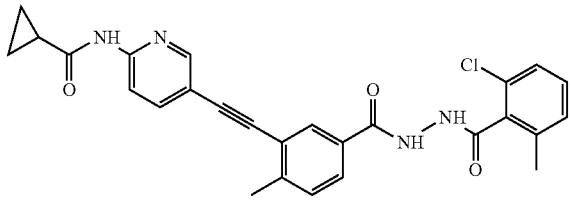

and a fusible polymeric carrier, wherein the mixture is an amorphous dispersion. The oral, solid dosage form optionally comprises of pharmaceutically acceptable excipients.

The amorphous dispersion in the oral solid dosage form of the invention is physically and chemically stable during melt processing and the oral, solid dosage form remains stable on storage. Particularly, when the oral dosage form is stored at 40° C. and 75% relative humidity for 6 months, each of the degradation impurity such as stage IV impurity and amine impurity is less than 0.2% by weight of the compound of formula I and the total impurity, which is a sum of known and unknown impurities, is less than 2% by weight of the compound of formula I. Further, the compound of formula I remains in the amorphous state during the period of storage.

DESCRIPTION OF THE PRESENT INVENTION

The present invention provides an oral, solid dosage form comprising a mixture of compound of formula I Formula I

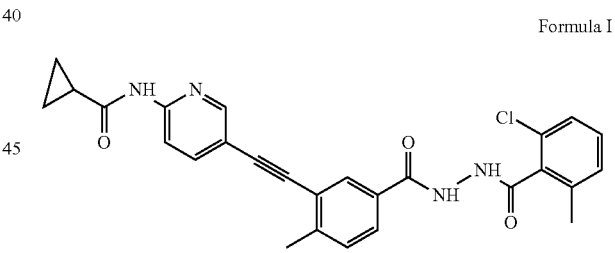

and a fusible polymeric carrier; and
optionally pharmaceutically acceptable excipients, wherein the mixture is an amorphous dispersion.

According to the present invention, the mixture of compound of Formula I and fusible polymeric carrier is an amorphous dispersion. The amorphous nature of the dispersion of compound of formula I in a fusible polymeric carrier may be determined by techniques known in the art. In one instance, the amorphous nature is determined by recording the X-ray Powder Diffraction (XRD) or by Differential scanning calorimetry analysis (DSC). The XRD spectrum of compound of formula showing the X-ray diffraction peaks characteristic of the crystalline form of compound of formula I is provided in FIG. 1. The XRD spectrum of fusible polymeric carrier namely, polyvinyl caprolactam-polyvinyl acetate-polyethylene glycol copolymer is provided in FIG. 2.

Figure 3:
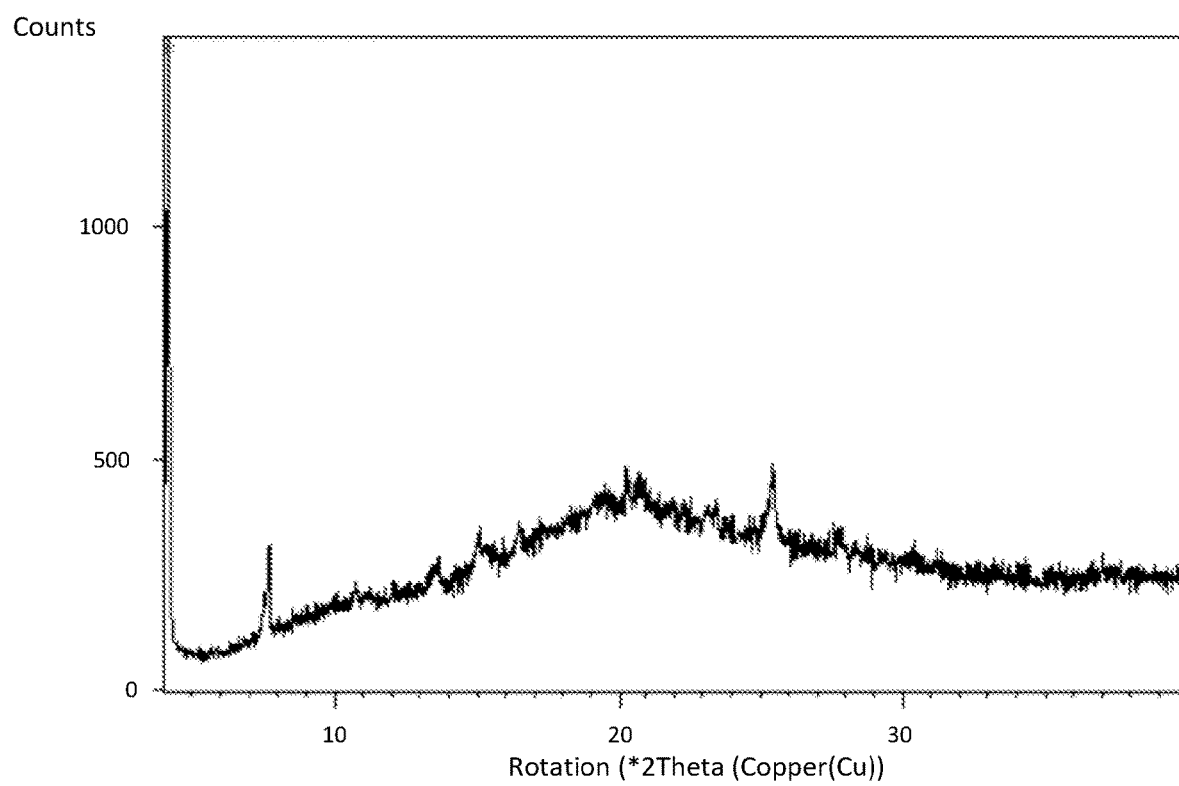
FIG. 3. X-ray diffraction of a physical mixture of fusible polymeric carrier, namely, polyvinyl caprolactam-polyvinyl acetate-polyethylene glycol copolymer and compound of formula I. The graph exhibits X-ray diffraction peaks characteristic of crystalline form of compound of formula I.
Figure 4:
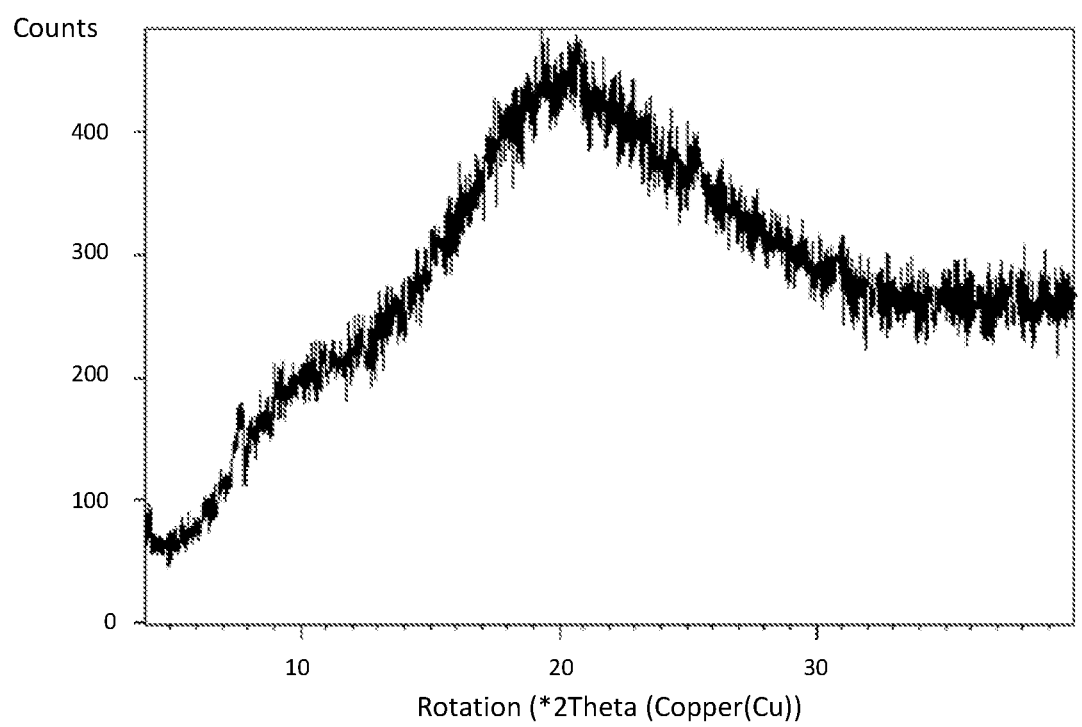
FIG. 4. X-ray Diffraction of amorphous dispersion of compound of formula I in a fusible polymeric carrier, namely, polyvinyl caprolactam-polyvinyl acetate-polyethylene glycol copolymer. The graph did not exhibit any X-ray diffraction peak characteristic of crystalline form of compound of formula I.

The term 'amorphous dispersion' as used herein means a dispersion of the active ingredient, compound of formula I in a fusible polymeric carrier that does not exhibit X-ray diffraction peaks characteristic of the crystalline form of compound of formula I. The XRD spectrum of amorphous dispersion of compound of formula I in fusible polymeric carrier is provided in FIG. 4 which shows absence of X-ray diffraction peaks characteristic of compound of formula I. In contrast, a physical mixture of compound of formula I and fusible polymeric carrier, exhibited X-Ray diffraction peaks characteristic of crystalline form of the active ingredient, compound of Formula I, as depicted in FIG. 3. FIG. 4 clearly shows the amorphous state of compound of formula I in a fusible polymeric carrier.

The term 'stable' or 'stability' as used herein means that the dosage form is physically and chemically stable. The 'chemically stable' means that the oral solid dosage form when stored at 40° C. and 75% relative humidity for 6 months, each of the degradation impurity such as stage IV impurity and amine impurity is less than 0.2% by weight of the compound of formula I and the total impurity, which is the sum of known and unknown impurities, is less than 2% by weight of the compound of formula I. The known degradation impurities of compound of formula I are named as stage IV impurity and amine impurity.

ethylene glycols having molecular weight of 1000 or more which are solid at room temperature, or mixtures thereof. According to an embodiment, the fusible polymer is polyethylene glycol having average molecular weight more than 1000 such as 1000, 2000, 1450, 1540, 2000, 3000, 3350, 4000, 4600, 8000 and mixtures thereof and the like. In one preferred embodiment, the fusible polymeric carrier is polyvinyl caprolactam-polyvinyl acetate-polyethylene glycol graft copolymer. It is soluble in water, acetone, methanol, ethanol and dimethylformamide; and is available in an average molecular weight in the range of 1,000 g/mol to about 5,000,000 g/mol. The polymer does not show any chemical degradation when melt processed. Preferably, the molecular weight is in the range from about 10,000 g/mol to about 500,000 g/mol. In one preferred embodiment the molecular weight is in the range from about 90,000 g/mol to about 140,000 g/mol. In yet another preferred embodiment, polyvinyl caprolactam-polyvinyl acetate-polyethylene glycol copolymer has a molecular weight in the range of from about 140,000 g/mol to 500,000 g/mol. According to one preferred embodiment of the invention, the amorphous dispersion is free of any other excipients. According to other embodiment, additional excipients may be present in the amorphous dispersion in limited amounts. The fusible polymeric carrier may be first selected by melt processing a

| Name of the impurity | Chemical Structure | Chemical Name |
|---|---|---|
| Stage IV impurity | 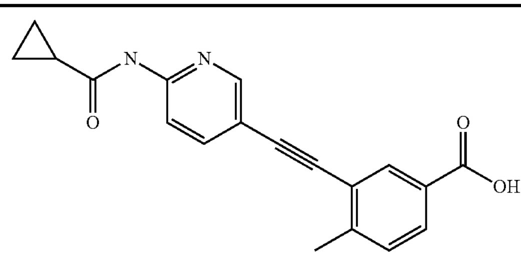 | 3-[6-(Cyclopropane carbonyl amino)pyridin-3-ylethynyl]-4-methyl benzoic acid |
| Amine impurity | 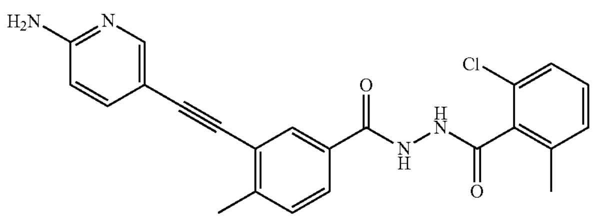 [SMILES: Cc1ccc(C(=O)NNC(=O)c2c(C)cccc2Cl)cc1C#Cc1ccc(N)nc1] | 2-Chloro-6-methyl-benzoic acid N'-[3-(6-amino-pyridin-3-ylethyny1)-4-methyl-benzoyl]hydrazide |

'Physically stable' means that when the oral solid dosage form of the present invention is stored at room temperature, the compound of formula I remains in an amorphous state.

The fusible polymeric carrier used in the amorphous dispersion of the oral solid dosage form of the present invention may be any fusible polymeric carrier that forms an amorphous dispersion with compound of formula I when the mixture of the fusible polymeric carrier and compound of formula I is processed by melt processing. According to one specific embodiment, the fusible polymeric carrier present in the amorphous dispersion of the present invention, is amphiphilic in nature and is soluble in aqueous medium as well as organic solvents such as alcohols, acetone, dimethylformamide and the like. Examples of such polymers include block copolymers of ethylene oxide and propylene oxide, polyvinyl caprolactam-polyvinyl acetate-polyethylene glycol copolymer, vinylpyrrolidone-vinyl acetate copolymer, poly-mixture of compound of formula I and the fusible polymeric carrier and performing a suitable test such as X-Ray Diffraction or Differential Scanning calorimetry to find that amorphous dispersion is formed. Those polymers when subjected to heating near the melting point of the compound of formula I degrade or decompose are not within the scope of the term 'fusible polymeric carrier'. Examples of such polymers include, but are not limited to, cellulose derivatives, such as for example, hydroxypropyl cellulose, hydroxypropyl methyl cellulose, hydroxypropyl methyl cellulose acetate succinate, hydroxypropyl methyl cellulose phthalate, acrylate polymers such as poly (methacrylic acid co-ethyl acrylate 1:1), poly (butylmethylacrylate co-dimethylaminoethyl methacrylate co-methyl methacrylate (1:2:1) and similar such polymers.

In one preferred embodiment, the amorphous dispersion contains compound of Formula I in the range from 0.1 to 30% by weight of the amorphous dispersion, for example 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30% by weight of the amorphous dispersion. The fusible polymeric carrier is present in the range from 10 to 99% by weight of the amorphous dispersion, for example 10, 20, 30, 40, 50, 60, 70, 80, 90, 95, 96, 97, 98, or 99% by weight of the amorphous dispersion. In one particular embodiment, the weight ratio of fusible polymeric carrier to compound of formula I is present in the range from 1 to 20, for example 1, 2, 3, 4, 5, 6, 7, 8, 9, 10, 11, 12, 13 and so on. Preferably, the weight ratio of fusible polymeric carrier to compound of formula I is present in the range from 4:1 to 14:1. More preferably, the weight ratio of fusible polymeric carrier to compound of formula I is about 7:1.

According to a preferred embodiment, the amorphous dispersion of fusible polymeric carrier and compound of formula I Formula I

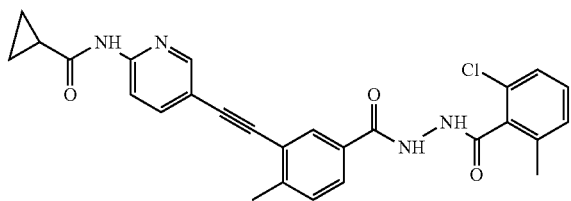

is prepared by a process of melting the mixture of the two components i.e. compound of Formula I and fusible polymeric carrier by a suitable technique such as hot melt extrusion.

The preferred methods of preparing the amorphous dispersion is melt processing, however it is also possible and within the scope of the present invention to prepare the amorphous dispersion by other methods as described herein. Melt process generally involves mixing the compound of formula I with a fusible polymeric carrier and heating to form a molten solution. According to another embodiment, the mixture of the fusible polymeric carrier and the compound of formula I may be heated to a temperature near the melting point of the fusible polymeric carrier while mixing or agitating to dissolve the compound of formula I in the molten fusible polymeric carrier. The hot melt solution is then cooled to obtain the amorphous dispersion. In another embodiment, the mixture of the compound of formula I and the fusible polymeric carrier is heated to a temperature near the melting points of the compound of formula I which has a melting point of 266±2° C. In another more particularly preferred embodiment, the amorphous dispersion may be obtained by hot melt extrusion. The fusible polymeric carrier is mixed with the therapeutically effective amount of compound of formula I and subjected to hot melt extrusion. The hot melt extrusion may be carried out by subjecting the mixture to gradual increase in temperature, starting from 100° C. to 300° C., followed by cooling at ambient temperature. According to the embodiments where the mixture is melted, the molten solution obtained may be cooled and solidified, and the solid mass is crushed and pulverized in a suitable mill to obtain the amorphous dispersion in the form of granules or powder.

According to another embodiment, the amorphous dispersion of the compound of formula I may also be prepared by dissolving the compound of formula I and fusible polymeric carrier in a common solvent and evaporating it until a clear, solvent free film is formed. Other method of preparation of amorphous dispersion is by dissolving the compound of formula I in a suitable liquid solvent and then incorporating the solution directly into the melt of a fusible polymeric carrier which is then evaporated until a clear, solvent free film is formed. The film may be further pulverized to suitable size by conventional techniques.

The amorphous dispersion obtained by any of the methods described above, is clear and transparent in appearance. The amorphous dispersion of the present invention is generally pulverized. The pulverization of the amorphous dispersion may be done by any conventional technique. The pulverized amorphous dispersion is free flowing and has acceptable compressibility. The bulk density of the pulverized amorphous dispersion of present invention is less than 0.7 g/ml, preferably 0.4, 0.5, 0.6 g/ml. In one specific embodiment, the bulk density is 0.52, 0.53, 0.54, 0.55, 0.56 g/ml.

In one embodiment, the amorphous dispersion is obtained in the solid form. The mass is pulverized using known techniques to obtain powder. The particle size of the pulverized amorphous dispersion may be less than 1000 microns, preferably, less than 750 microns, most preferably, less than 500 microns. In one specific embodiment, the particle size is in the range of about 75 microns to 425 microns. In one preferred embodiment, the size of the pulverized amorphous dispersion is below 600 microns, preferably below 425 microns and more preferably below 180 microns. Preferably, the size of the particles is below 425 microns. According to an embodiment, about 100% of the particles of the pulverized amorphous dispersion are of size less than 425 microns. According to another embodiment, about 85% of the particles are of size less than 250 microns. According to one another embodiment, about 65% of the particles are of size less than 180 microns. According to one another embodiment, about 45% of the particles are of size less than 150 microns. According to yet another embodiment, about 15% of the particles are of size less than 75 microns.

In one specific embodiment, the present invention provides an oral, solid dosage form comprising a mixture of compound of formula I Formula I

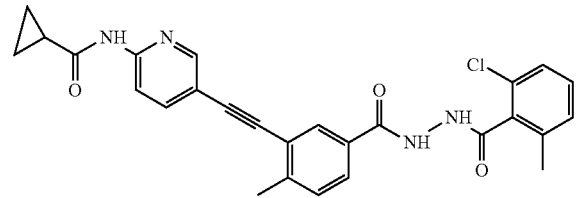

and a fusible polymeric carrier; and
optionally pharmaceutically acceptable excipients, wherein
the mixture is an amorphous dispersion, further wherein
the fusible polymeric carrier is polyvinyl caprolactam-polyvinyl acetate-polyethylene glycol graft co-polymer. In a preferred embodiment, the weight ratio of the fusible polymeric carrier to compound of formula I is about 7:1. Generally, the amorphous dispersion is in the micronized form. The amorphous dispersion when in the pulverized form, all the particles have size less than 750 microns, preferably less than 500 microns.

In one another specific embodiment, the present invention provides an oral, solid dosage form comprising a mixture of compound of formula I

Formula I

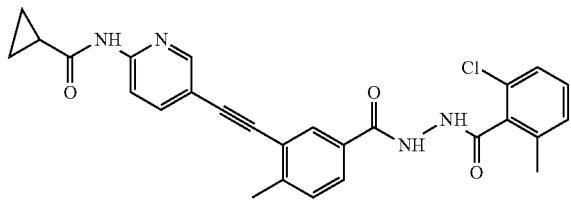

and a fusible polymeric carrier; and optionally pharmaceutically acceptable excipients, wherein the mixture is an amorphous dispersion, further wherein the fusible polymeric carrier may be polyvinyl caprolactam-polyvinyl acetate-polyethylene glycol graft copolymer. In preferred embodiment, the weight ratio of the fusible polymeric carrier to compound of formula I is about 7:1. Generally, the amorphous dispersion is in the micronized form. The amorphous dispersion when in the pulverized form, all the particles have size less than 750 microns, preferably less than 500 microns. It may be noted that the fusible polymeric carrier is not a polymer which melts with degradation or decomposition when heated near the melting point of compound of formula I. The examples of polymers that degrade or decompose substantially when subjected to melting or heating at the temperature near the melting point of compound of formula I, include, but are not limited to, cellulose derivatives, such as for example, hydroxypropyl cellulose, hydroxypropyl methyl cellulose, hydroxypropyl methyl cellulose acetate succinate, hydroxypropyl methyl cellulose phthalate, acrylate polymers such as poly (methacrylic acid co-ethyl acrylate 1:1), poly (butylmethylacrylate co-dimethylamino ethyl methacrylate co-methyl methacrylate (1:2:1) and similar such polymers.

In yet another specific embodiment, the present invention provides an oral, solid dosage form comprising a mixture consisting essentially of compound of formula I

Formula I

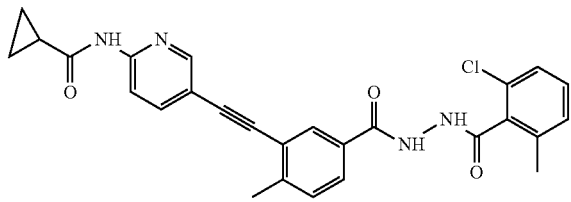

and a fusible polymeric carrier; and optionally pharmaceutically acceptable excipients, wherein the mixture is an amorphous dispersion, further wherein the fusible polymeric carrier may be polyvinyl caprolactam-polyvinyl acetate-polyethylene glycol graft copolymer. In this embodiment, the amorphous dispersion which is a mixture of compound of formula I and fusible polymeric carrier contains only the fusible polymeric carrier and is free of any other excipient or polymer which was found to degrade or decompose when subjected to heating near the melting point of compound of formula I. Such polymers or excipients include, but are not limited to, cellulose derivatives such as for example, hydroxypropyl cellulose, hydroxypropyl methyl cellulose, hydroxypropyl methyl cellulose acetate succinate, hydroxypropyl methyl cellulose phthalate, acrylate polymers such as poly (methacrylic acid co-ethyl acrylate 1:1), poly (butylmethylacrylate co-dimethylamino ethyl methacrylate co-methyl methacrylate (1:2:1) and like.

In preferred embodiment, the weight ratio of the fusible polymeric carrier to compound of formula I is about 7:1. Generally, the amorphous dispersion is in the micronized form. The amorphous dispersion when in the pulverized form, all the particles have size less than 750 microns, preferably less than 500 microns.

In one another specific embodiment, the present invention provides an oral, solid dosage form comprising a mixture consisting of compound of formula I Formula I

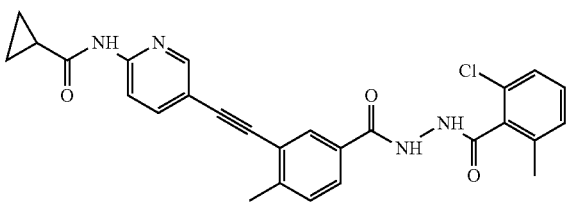

and a fusible polymeric carrier; and optionally pharmaceutically acceptable excipients, wherein the mixture is an amorphous dispersion, further wherein the fusible polymeric carrier may be polyvinyl caprolactam-polyvinyl acetate-polyethylene glycol graft copolymer. Alternatively, the amorphous dispersion is a mixture comprising compound of formula I Formula I

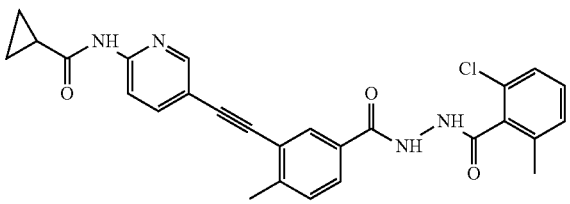

and a fusible polymeric carrier wherein the mixture is substantially free of excipients which were found to degrade or decompose when subjected to heating near the melting point of the compound of formula I.

The amorphous dispersion of the compound of Formula I and fusible polymeric carrier may be directly compressed into tablets or filled into a capsule, sachet or pouch. More preferably, the amorphous dispersion is converted into tablets or capsules using pharmaceutically acceptable excipients. Methods used include, conventional methods such as those where the amorphous dispersion is mixed with the pharmaceutically acceptable excipients and converted into tablets by direct compression or converted into capsules by filling the mixture into capsules or alternatively converted into granules by wet granulation or dry granulation and the granules filled into capsules or compressed into tablets. The oral, solid dosage form of the present invention may be obtained by mixing the amorphous dispersion obtained by any one of the above methods with other conventional excipients like disintegrants, wicking agents, lubricants, surfactants, buffers, diluents and converting the mixture to an oral, solid dosage form, for example it may be filled into hard gelatin capsule, pouches, sachets, or compressed into tablets. According to an embodiment, the oral, solid dosage form is a hard gelatin capsule filled with the milled amorphous dispersion comprising compound of formula I and polyvinyl caprolactam-polyvinyl acetate-polyethylene glycol copolymer as the fusible polymeric carrier. According to another embodiment, the oral solid dosage form is a compressed tablet comprising the milled amorphous dispersion of compound of formula I and polyvinyl caprolactam-polyvinyl acetate-polyethylene glycol copolymer as the fusible polymeric carrier and other conventional pharmaceutical excipients. In one preferred embodiment, these filled hard gelatin capsules or tablets are packed in closed containers with a desiccant and are stored at 25° C. and 60% relative humidity.

The oral solid dosage form of the present invention is physically stable. That is the compound of formula I remains in the amorphous state and does not get converted into crystalline state during its shelf life when stored at ambient conditions. The amorphous nature of compound of Formula I in the oral solid dosage form may be determined by either X-ray diffraction or differential scanning calorimetric analysis (DSC). The XRD spectrum of crystalline form of compound of formula I shows characteristic diffraction peaks. The XRD of the oral solid dosage form of the present invention does not show diffraction peaks characteristic of crystalline compound of formula I at initial time point as well as upon storage at 40° C. and 75% relative humidity for 9 months. In order to confirm the amorphous nature, the XRD of the placebo excipient blend is also recorded. The absence of characteristic, diffraction peaks in the XRD spectrum, which are characteristic of crystalline compound of formula I proves that the compound of formula I is in the amorphous state in the oral solid dosage form of the present invention upon storage.

The oral solid dosage form of the present invention is also chemically stable. This means that, each of the degradation impurity such as stage IV impurity and amine impurity is less than 0.2% by weight of the compound of formula I. Also the total impurity, which is sum of known and unknown impurities, is less than 2% by weight of the compound of formula I. In a preferred embodiments, each of the degradation impurity such as stage IV impurity and amine impurity is less than 0.2%, preferably in the range of 0.001 to 0.15%, preferably, 0.01 to 0.1% by weight of the compound of formula I. Also, the total impurities are less than 2%, preferably, less than 0.001 to 1.5% or 0.01 to 1% by weight of the compound of Formula I.

Further, the amorphous dispersion provided an improved oral bioavailability in that the rate and extent of absorption of compound of formula I was significantly enhanced as compared to the plasma levels when the crystalline form of compound of formula I in a vehicle was administered to dogs. The enhancement in bioavailability was significant i.e. it was found to be in magnitude of about 20, 30, 40, 50 times higher as compared to the bioavailability obtained when the crystalline form of compound of formula I in a vehicle was administered orally. Thus, the oral, solid dosage of the present invention was not only stable both chemically and physically, but was also made orally bioavailable.

The pharmaceutically acceptable excipients are the ones that are used conventionally and are known in the art. These include diluents, disintegrants, wicking agents and surfactants. Examples of disintegrating agents used include, but are not limited to, natural starch, pregelatinized starch, sodium starch glycolate, microcrystalline cellulose, methylcellulose, croscarmellose, cross-linked cellulose, cross-linked sodium carboxymethylcellulose, cross-linked carboxymethylcellulose, cross-linked croscarmellose, cross-linked starch, sodium starch glycolate, crospovidone, cross-linked polyvinylpyrrolidone, alginic acid, sodium alginate, magnesium aluminum silicate, agar, guar, locust bean, karaya, pectin, tragacanth, sodium starch glycolate, bentonite, cation-exchange resin, sodium lauryl sulfate, or in combination thereof. In an embodiment, disintegrant used in oral solid dosage form is present in an amount ranging from about 1% to 10% of the total weight of the oral solid dosage form. In an embodiment, surfactant used in oral solid dosage form is present in an amount ranging from about 0.1% to 10% of the total weight of the oral solid dosage form. Lubricants or glidants used in the oral solid dosage form are selected from group consisting of, but are not limited to, silicon dioxide, stearic acid, calcium hydroxide, talc, corn starch, sodium stearyl fumarate, alkali-metal and alkaline earth metal salts, stearic acid, sodium stearates, magnesium stearate, zinc stearate, waxes, boric acid, sodium benzoate, sodium acetate, sodium chloride, leucine, polyethylene glycol, methoxypolyethylene glycol, polyethylene glycol 4000, polyethylene glycol 5000, polyethylene glycol 6000, propylene glycol, sodium oleate, glyceryl behenate, glyceryl palmitostearate, glyceryl benzoate, magnesium or sodium lauryl sulfate, and the like. The glidant used in oral solid dosage form is present in an amount ranging from about 0.1% to 3% of the total weight of the oral solid dosage form. Diluents used in oral solid dosage form are selected from the group consisting of, but are not limited to lactose, starch, mannitol, sorbitol, dextrose, microcrystalline cellulose, dibasic calcium phosphate, dicalcium phosphate dehydrate, tricalcium phosphate, calcium phosphate, anhydrous lactose, spray-dried lactose, pregelatinized starch, compressible sugar, mannitol, hydroxypropylmethylcellulose, hydroxypropylmethylcellulose acetate stearate, sucrose-based diluents, sugar, monobasic calcium sulfate monohydrate, calcium sulfate dehydrate, calcium lactate trihydrate, dextrates, hydrolyzed cereal solids, amylose, powdered cellulose, calcium carbonate, glycine, kaolin, mannitol, sodium chloride, inositol, bentonite, silicified microcrystalline cellulose and combination thereof. The diluent used in oral solid dosage form is present in an amount ranging from about 1% to 90% of the total weight of the oral solid dosage form.

The invention will now be further described by the following examples, which are illustrative rather than limiting.

EXAMPLE I and II

TABLE 1

Composition of the amorphous dispersion

| INGREDIENTS | EXAMPLE I (% by weight) | EXAMPLE II (% by weight) |
|---|---|---|
| Compound of Formula I | 12 | 10.9 |
| Polyvinyl caprolactam-polyvinyl acetate-polyethylene glycol co-polymer | 88 | 80 |

TABLE 1-continued

Composition of the amorphous dispersion

| INGREDIENTS | EXAMPLE I (% by weight) | EXAMPLE II (% by weight) |
|---|---|---|
| Block copolymer of polyethylene and polypropylene (LUTROL F 68) Where x = approx. 79 and y = approx. 28; proportion of weight of polyoxyethylene is approx. 80%. | — | 9.1 |

The specified amounts of compound of formula I and polyvinyl caprolactum-polyvinyl acetate-polyethylene glycol co-polymer were sifted and mixed in a blender (Example II additionally included LUTROL F 68). The resulting blend was then charged to a hot melt extruder gradually to a higher temperature (100° C. to 200° C.) yielding the melt extrudates. The extrudates were then milled in a comminuting mill fitted with 4.00 mm screen at 2000-2400 RPM which was sifted through ASTM #40 and loaded in a blender. The final content was collected in a suitable container.

The extrudates were subjected to X-Ray Diffraction. It was observed that the powder X-Ray Diffraction of melt extrudates of Example I (FIG. 4) did not exhibit any peaks characteristic of crystalline form of compound of formula I, confirming its amorphous nature.

EXAMPLE III

Suitable amount of amorphous dispersion of Example I and the crystalline form of compound of formula I suspended in a vehicle were administered orally to dogs. Blood samples were withdrawn at various time intervals and the plasma levels of compound of formula I were recorded. The $C_{max}$, $AUC_{0\ to\ t}$ and $AUC_{0-\infty,\ in\ in}$ plasma are tabulated below.

TABLE 2

Bioavailability data

| Pharmacokinetic parameters | Compound of formula I in a vehicle | Amorphous dispersion of Example I |
|---|---|---|
| $C_{max}$ (ng/ml) | 41 | 780 |
| $AUC_{0\ to\ t}$ (hr*ng/mL) | 290 | 8758 |
| $AUC_{0\ to\ \infty}$ (hr*ng/mL) | 388 | 11492 |

From the above table, it is evident that the oral administration of amorphous dispersion comprising compound of Formula I, showed significantly higher oral bioavailability ($C_{max}$, $AUC_{0\ to\ t}$ & $AUC_{0\ to\ \infty}$) of compound of formula I as compared to test which did not include the compound of formula I as an amorphous dispersion with fusible polymeric carrier, namely polyvinyl caprolactam-polyvinyl acetate-polyethylene glycol co-polymer, but was simply dispersed in a vehicle. The oral bioavailability was increased to about thirty times when same amount of compound of formula I was orally administered.

EXAMPLE IV

The amorphous dispersion in the form of extrudates of Example I was mixed with other conventional excipients like disintegrants, wicking agents, surfactants, lubricants, buffers, diluents and was filled into hard gelatin capsules of appropriate size to the target fill weight. The filled capsules were packed into high density polyethylene bottles of appropriate capacity with desiccant and child resistant closures. These capsules were subjected to accelerated stability conditions at 40° C. and 75% relative humidity for 6 months. The impurities and related substances were measured before (initial) and after storage. The levels of impurities in both before storage and after storage at 40° C. and 75% relative humidity for 6 months were below the quantifiable limits. The stability study data showed that degradation impurities like stage IV impurity, amine impurity, highest unknown impurity and total impurities were well within the acceptable limits. This demonstrated that the amorphous dispersion of compound of formula I in the form of oral solid dosage form was chemically stable.

Figure 1:
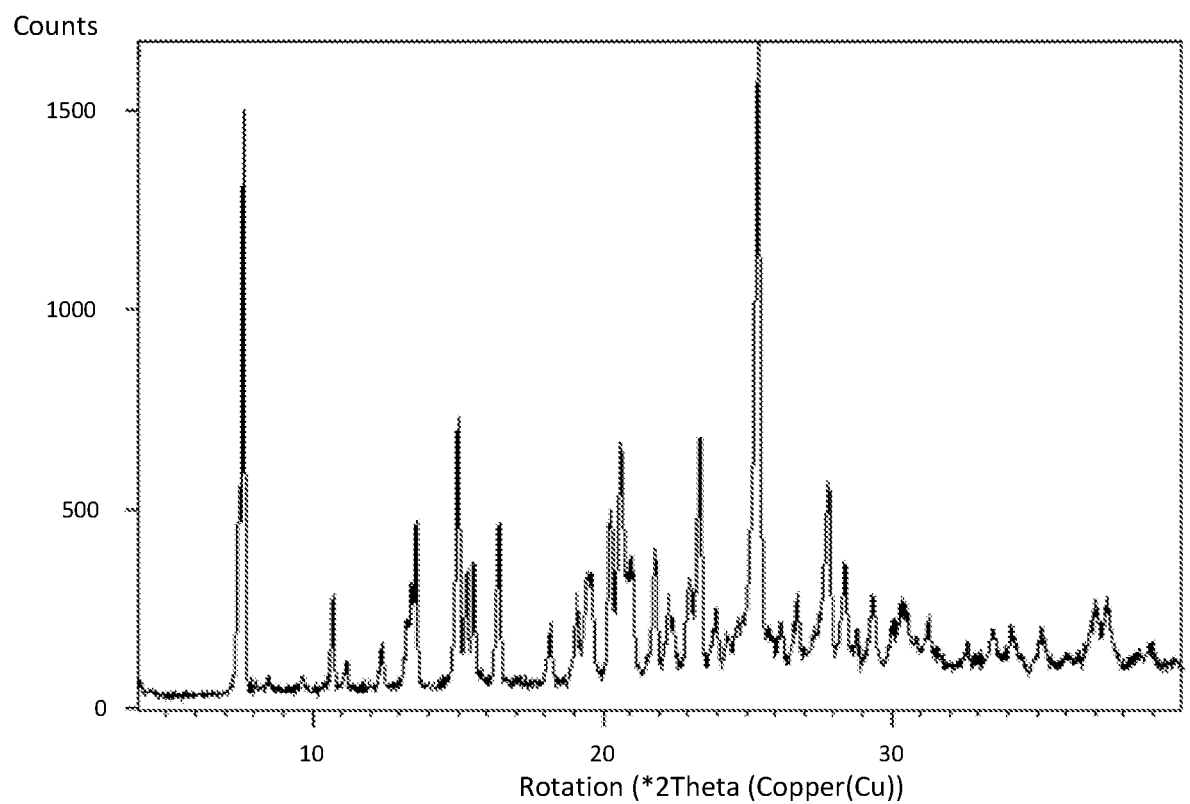
FIG. 1. X-ray diffraction exhibits peaks characteristic of crystalline form of compound of formula I.
Figure 2:
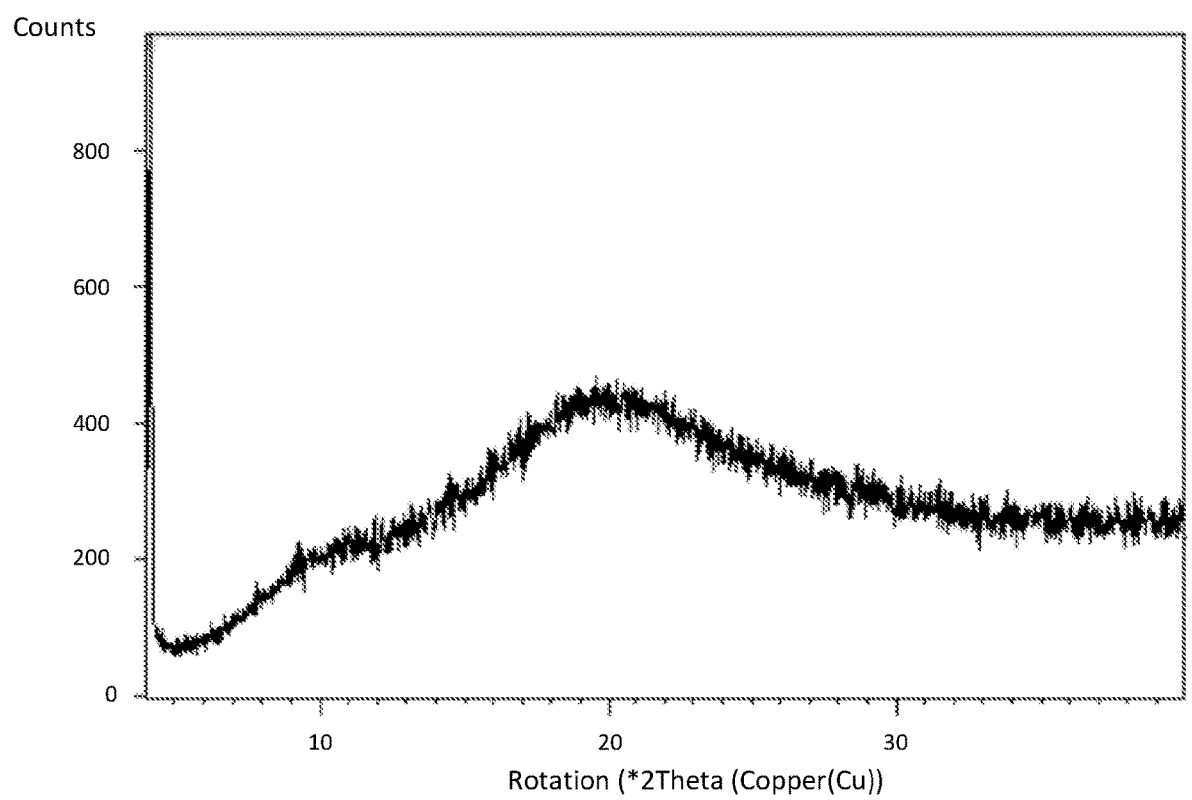
FIG. 2. X-ray diffraction of a fusible polymeric carrier, namely, polyvinyl caprolactam-polyvinyl acetate-polyethylene glycol copolymer.

The blend of capsule stored at 40° C. and 75% relative humidity for 9 months in closed container with a desiccant was subjected to XRD analysis. Also the placebo excipients blend of capsule without compound of formula I was subjected to XRD analysis to rule out the interference of the excipients or the fusible polymeric carrier. The XRD of crystalline form of compound of formula I is provided in FIG. 1 showing characteristic peaks of crystalline form of compound of formula I. These peaks were absent in the XRD spectrum of blend of capsule taken before storage and after it was stored at 40° C. and 75% relative humidity for 9 months. This demonstrated that the compound of formula I remained in amorphous state on storage throughout its shelf life, i.e. it was physically stable upon storage.

The invention claimed is:

1. An oral, solid dosage form comprising a mixture of compound of formula I

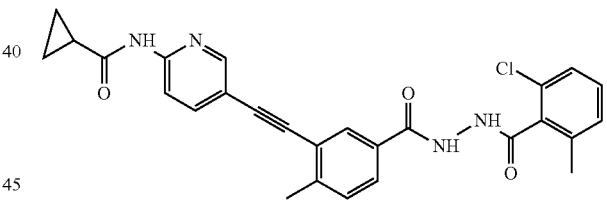

Formula I and a fusible polymeric carrier; and
optionally pharmaceutically acceptable excipients,
wherein the mixture is an amorphous dispersion.

2. The oral, solid dosage form as claimed in claim 1, wherein the fusible polymeric carrier is polyvinyl caprolactam-polyvinyl acetate-polyethylene glycol graft co-polymer.

3. The oral, solid dosage form as claimed in claim 2, wherein the amorphous dispersion is in the pulverized form wherein all the particles have size less than 500 microns.

4. The oral, solid dosage form as claimed in claim 1, wherein the weight ratio of the fusible polymeric carrier to compound of formula I is about 7:1.

5. The oral, solid dosage form as claimed in claim 3, wherein the dosage form is a capsule filled with the amorphous dispersion and pharmaceutically acceptable excipient.

* * * * *